United States Patent [19]
Wood et al.

[11] Patent Number: 6,084,717
[45] Date of Patent: Jul. 4, 2000

[54] LASER BEAM SPLITTER

[75] Inventors: Leroy M. Wood, Buffalo; William R. Potter, Grand Island, both of N.Y.

[73] Assignee: Health Research, Inc., Buffalo, N.Y.

[21] Appl. No.: 09/368,274

[22] Filed: Aug. 3, 1999

[51] Int. Cl.[7] .......................... G02B 27/10; G02B 27/14; G02B 5/30

[52] U.S. Cl. .......................... 359/629; 359/618; 359/627; 359/633; 359/495; 606/18

[58] Field of Search .................................. 359/627, 629, 359/633, 634, 618, 495, 196; 33/DIG. 21; 606/18; 372/99, 107

[56] References Cited

U.S. PATENT DOCUMENTS

| | | | |
|---|---|---|---|
| 4,988,630 | 1/1991 | Chen et al. | 436/533 |
| 5,048,946 | 9/1991 | Sklar et al. | 351/206 |
| 5,325,381 | 6/1994 | Paoli | 359/495 |
| 5,798,867 | 8/1998 | Uchida et al. | 359/629 |
| 5,948,291 | 9/1999 | Neylan et al. | 219/121.17 |

*Primary Examiner*—Georgia Epps
*Assistant Examiner*—Saeed Seyrafi
*Attorney, Agent, or Firm*—Michael L. Dunn

[57] ABSTRACT

An apparatus that efficiently and accurately splits a laser beam input into eight or more outputs where the beam energies of the output beams are within ten and preferably within five percent of each other. The apparatus includes an arrangement of at least seven beam splitters each of which can split an incident laser beam into two exit beams of equal energy at a particular incident angle. At least some of the splitters have different particular incident angles but the particular incident angle of the first splitter is used as the incident angle for all splitters. The exit beams of the first splitter are directed to second and third splitters that have particular incident angles relatively close to the particular incident angle of the first splitter when compared with the relationship of the particular incident angle of the first splitter to the particular incident angles of the remaining splitters.

25 Claims, 6 Drawing Sheets

EIGHT BEAMS

EIGHT BEAMS

FOUR BEAMS

TWO BEAMS ns as ta6,084,717

LASER BEAM SPLITTER

BACKGROUND OF THE INVENTION

This invention relates to laser light and more particularly relates to beam splitters for splitting an input laser beam from a single source into multiple output laser beams. The invention more particularly relates to such beam splitters having output beams suitable for being directed to a fiber optic coupler and the use of beams from the fiber optics for therapeutic treatment, such as photodynamic therapy where an undesirable area on a patient, e.g. a tumor, is exposed to a laser beam after absorption by the tumor of a photosensitizing agent such as a porphyrin derivative. More particularly photodynamic therapy is based upon accumulation in tumors of a photosensitizing drug that is activated by visible light to produce a locally cytotoxic agent. For example PHOTOFRIN®, a porphyrin derivative approved for clinical use in the United States, Canada, Europe, and Japan, is activated by 630 nm light. Typically, light emitted from a tunable laser is delivered to a lesion by an optical fiber.

A problem associated with laser medical procedures, e.g. photodynamic therapy, is that often numerous areas on the same patient in fact require treatment. Time involved in setting up and individually treating each of the numerous areas by a single laser source can be extensive often exceeding the useful life of injected photosensitizing compound. Further, sequential treatment results in high cost due to time involved for trained personnel and inefficient use of costly equipment as well as significant discomfort on the part of the patient. It is of course possible to provide multiple laser generators so that multiple areas can be simultaneously treated. Unfortunately, however, the cost for providing multiple laser generators for a single patient treatment is prohibitive.

It is known that laser beams can be split by beam splitters that comprise a partially reflective and partially transparent surface so that an incident laser beam is partially reflected and partially transmitted so that the beam is effectively split into two parts. Unfortunately, there has been no way to practically, consistently or economically commercially manufacture such surfaces so that they all will reflect 50 percent of the beam energy and transmit 50 percent of the beam energy at the same particular incident angle (the angle of the beam to the surface that splits the beam energy in half).

The manufacture of a beam splitter apparatus for more than two output beams thus would have been very difficult since the manufacturing process would have to take the particular incident angle of each individual beam splitter into consideration which requires the calculation of numerous angles of reflection and resulting various alignments and does not permit the use of any kind of standardized set angle hardware within the apparatus. The assembly of such a multiple beam splitter thus would have been tedious, time consuming and unacceptably expensive.

It has thus not been possible to easily and inexpensively manufacture a beam splitter to form four or more output beams where the output beam energies are within ten percent of each other and certainly not within five percent or less of each other.

BRIEF DESCRIPTION OF THE INVENTION

Figure 1:
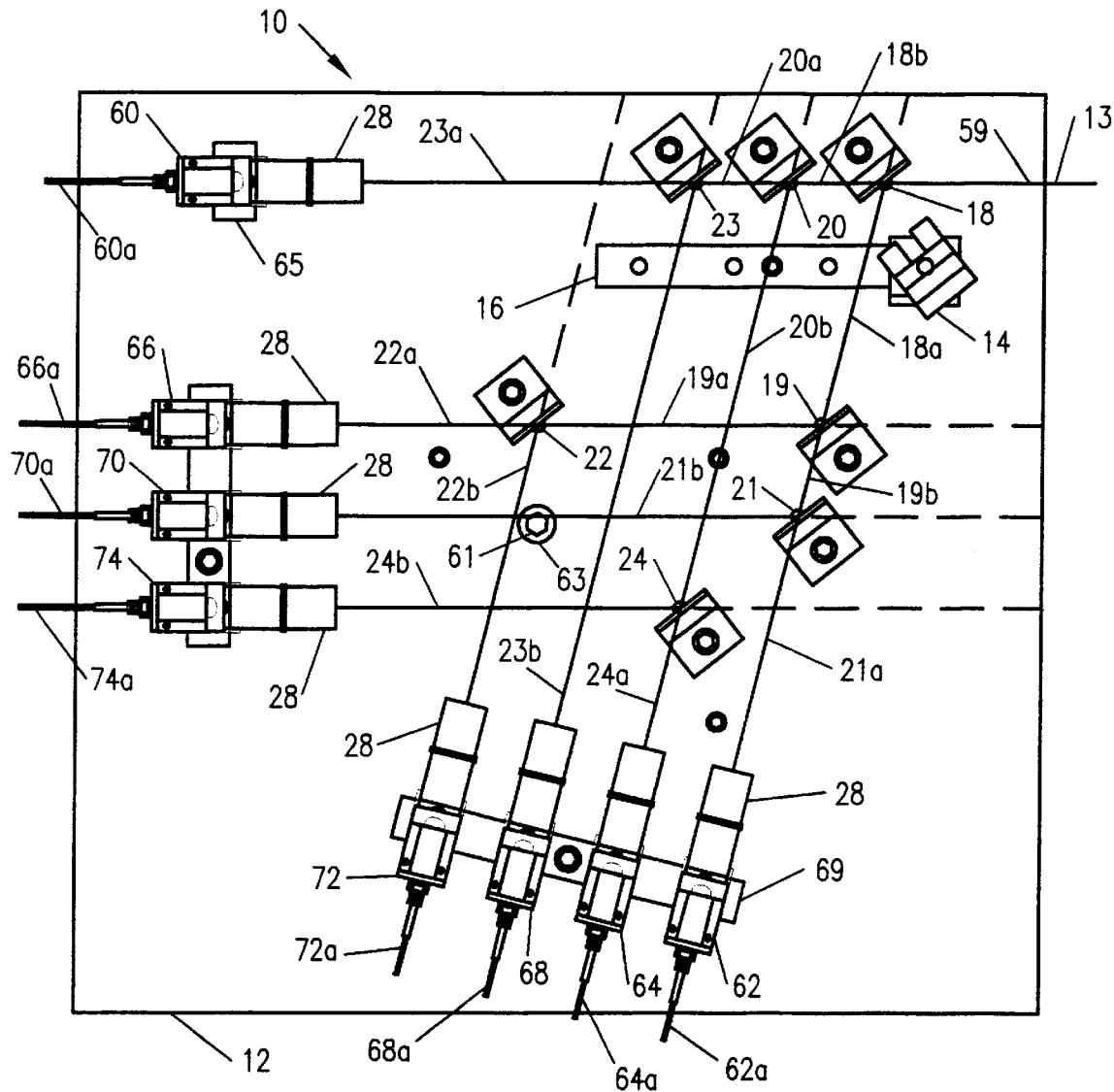
FIG. 1 shows a top view of an embodiment of the invention arranged to provide eight output beams.

In accordance with the invention an apparatus is therefore provided to efficiently and accurately split a laser beam input into eight or more outputs where the beam energies of the output beams are within ten and preferably within five percent of each other. More particularly, the invention comprises a laser beam splitter apparatus capable of forming at least eight output laser beams from a single laser input, where the apparatus has the following described structure.

The apparatus includes an arrangement of at least seven beam splitters each of which splits an incident laser beam into two exit beams of equal energy at a particular incident angle for each splitter. At least some of the particular incident angles are different from each other for the different splitters. The apparatus includes a first splitter, having a first splitter particular incident angle, and arranged to receive the laser beam input at the first particular incident angle and to provide two exit beams.

The second and third splitters have second and third particular incident angles, and are arranged so that the exit beams of the first splitter are directed to the second and third splitters, as their incident laser beams also at the first particular incident angle. The second and third splitters each provide two exit beams when receiving an incident laser beam.

The fourth, fifth sixth and seventh splitters, respectively have fourth, fifth, sixth and seventh particular incident angles, and are arranged so that the exit beams from said second and third splitters are directed to the fourth, fifth, sixth and seventh splitters at the first particular incident angle to provide their incident laser beams. Each of the fourth, fifth, sixth and seventh splitters provide two exit laser beams when receiving an incident laser beam to provide an apparatus output of at least eight beams.

In accordance with the invention, the second and third particular incident angles are closer to the first particular incident angle than the fourth, fifth, sixth and seventh particular incident angles. The variance in energy between the two exit beams of each of the first, second and third splitters are less than about 3 percent (preferably less than about one percent) at an incident laser beam angle about equal to the first particular incident angle and the variance in energy between the two exit beams of each of the fourth, fifth, sixth, and seventh splitters are less than about 7 percent (preferably less than about 5 percent) at an incident laser beam angle about equal to the first particular incident angle. The apparatus is capable of providing at least eight output beams varying in energy from each other by less than about 7 percent, preferably less than 5 percent, and most preferably, less than about 3 percent. The apparatus of the invention, by its design, permits the use of splitters having variable particular incident angles, assembled at a single first incident angle used on all splitters, without unacceptable compounding of errors, e.g. as might occur if splitters having the greatest deviation in particular incident angles from each other were used in the first series. Because the beam first is split by splitters with the smallest variance in particular incident angles, the compounding of splitting errors is minimized.

The apparatus of the invention may further include additional beam splitters for receiving the output beams from the fourth, fifth, sixth and seventh splitters to provide a total number of output beams from the apparatus in excess of eight. For example, eight additional beam splitters may be provided to receive the output from the fourth, fifth, sixth and seventh splitters to provide a total of sixteen apparatus output beams. In such a case the beam splitters are arranged as above described, except that the particular angles of the additional eight splitters vary from the first incident angle by more than the particular incident angles of the fourth, fifth, sixth and seventh splitters. The particular incident angles of the additional eight splitters, nevertheless, still vary the first particular incident angle so that the power outputs vary by less than seven percent.

Most desirably, the variance in energy between the two exit beams of each of the first, second and third splitters is less than about 0.5 percent at an incident laser beam angle about equal to the first particular incident angle and the variance in energy between the two exit beams of each of the fourth, fifth, sixth, and seventh splitters being less than about 1.5 percent at an incident laser beam angle about equal to the first particular incident angle and the apparatus is capable of providing at least eight output beams varying in energy from each other by less than about 3 percent.

In a preferred embodiment of the invention, the apparatus further includes an adjustable redirecting means for intercepting said laser input and redirecting it away from the first splitter. The redirecting means may, for example, be adjusted to redirect the laser input away from all splitters to provide an apparatus output of a single laser beam. The redirecting means may also be adjusted for intercepting the laser input to redirect it toward one of the fourth, fifth, sixth and seventh splitters to provide an apparatus output of two laser beams or may be adjusted for intercepting said laser input to redirect it toward one of the second and third splitters to provide an apparatus output of four laser beams.

The redirecting means usually includes a repositionable mirror but may employ a prism rather than a mirror for redirecting the input laser beam. A mirror is usually preferred because it can usually redirect a beam with less energy loss than a prism. In a preferred embodiment, the redirecting means is a front surface mirror having at least four adjustable positions wherein:

a) position one intercepts the laser input to reflect the beam away from the splitters to provide an apparatus output of a single laser beam;
b) position two intercepts the laser beam to reflect it toward one of the fourth, fifth, sixth, and seventh splitters to provide an apparatus output of two laser beams;
c) position three intercepts the laser beam to reflect it toward one of the second and third splitters to provide an apparatus output of four laser beams; and
d) position four permits the input beam to strike the first splitter at the first splitter particular incident angle to provide an apparatus output of eight laser beams. Position four may either reflect the input to the first splitter at the first splitter incident angle or may be moved out of the path of the input beam which is aligned to strike the first splitter at the first splitter incident angle.

When the energy of the apparatus output laser beams is to be directed to and carried by fiber optics, fiber optic couplers are provided in paths of the apparatus output laser beams to receive the energy of such beams and for directing beam energy through a fiber optic. The use of such couplers provide an unexpected advantage in that the couplers provide a back reflection beam having an energy of from about 2 to about 6 percent, usually about 4 percent, of the energy received from an output beam. A means for aligning the output beams with the couplers can therefore be provided by varying the position of the couplers relative to an image formed by their back reflection beams.

The invention further includes a method for providing laser treatment to a patient by simultaneously directing a plurality of laser beams from fiber optics receiving laser energy from the apparatus of the invention to areas on a patient in need of laser treatment. For example, the apparatus of the invention may be used as at least a part of a light delivery system for photodynamic therapy, e.g., in conjunction with fiber optic positioners as disclosed in U.S. Pat. No. 5,671,317.

DETAILED DESCRIPTION OF THE INVENTION

"Laser beam" as used herein means a single frequency coherent beam of light. "Light" means any electromagnetic radiation within the ultraviolet, visible and near infrared ranges. "Beam" means light energy of a specific, essentially non-spreading cross sectional area that travels in an essentially straight line direction in a vacuum.

"Splitter" means a device that divides a beam into two beams that travel in different directions. "Splitters" are usually partially transparent mirrors that reflect a part of the beam energy and transmit a part of the beam energy to form two beams. "Incident laser beam" means a beam that strikes a splitter at a particular incident angle and is the beam being split. "Exit laser beam" means the two beams exiting a splitter. "Beam Splitter apparatus" means an apparatus for splitting laser beams that includes two or more splitters. "Laser input" or "input beam" means a beam to be split that enters a beam splitter apparatus. "Output laser beam" means a beam exiting a beam splitter apparatus after having been split from an input beam. "Particular incident angle" means an angle of incidence to a surface of a beam splitter that will divide a beam striking the splitter at that angle into two beams having essentially equal energy.

The invention may be illustrated by reference to the following preferred embodiment.

A beam splitter apparatus or device was designed and constructed to split the output of an argon-laser pumped dye laser into up to eight beams of essentially equal power, i.e., within about 10 percent of each other, preferably within about 5 percent of each other and most preferably within about 3 percent of each other. The power from each beam could be independently varied when necessary. The beam splitter device of this preferred embodiment is compact and of simple, low cost construction. Beam splitter mounts, attenuators and fiberoptic coupler bodies were designed and fabricated specifically for the apparatus. Other components were obtained commercially.

The beam splitter apparatus divides a dye-laser beam into eight beams of essentially equal power with negligible loss in total power. The device also allows four, two or one output(s), each of which may be coupled to an optical fiber for the delivery of therapeutic light to an individual treatment field. Means to control the power of the individual beams were provided, e.g. in the form of attenuators, in order to equalize the treatment powers when optical fibers of different efficiencies were used, or when the treatment plan required dissimilar power outputs from each fiber. The apparatus is compact which is especially desirable because space is at a premium in clinics and laboratories.

The beam splitter apparatus 10 of the preferred embodiment is shown in FIGS. 1–4. The optical components were mounted on a 16-inch by 18-inch by ½-inch aluminum jig plate which serves as an optical table 12. The table 12 can be translated on a 12-inch optical rail (not shown) from the 8-beam position to a second position where the dye laser beam 13 is intercepted by a plane fold mirror 14. The fold mirror is translated on a microrail 16 parallel to the dye laser beam. When the fold mirror is at a position where the reflected beam duplicates a segment of a ray path of the 8-beam alignment, a 4-beam output (FIG. 2), 2-beam output (FIG. 3) or a 1-beam output (FIG. 4) is produced.

Light beams 18a, 18b, 19a, 19b, 20a, 20b, 21a, 21b, 22a, 22b, 23a, 23b, 24a, 24b, reflected by, or transmitted through, the splitters 18–24, when coupled to an optical fiber 60a, 62a, 64a, 66a, 68a, 70a, 72a or 74a, for photodynamic therapy, ultimately pass through Brewster-window type attenuators 28 that allow between 20 and 100% transmittance. The light is then focused by a plano-convex lens 50 (see FIG. 6) onto the flat, polished surface of a quartz optical fiber 60a, 62a, 64a, 66a, 68a, 70a, 72a or 74a. Depending on the treatment plan, optical fibers are usually either 200, 400 or 600 μm diameter.

Commercial beam splitters are designed for a 45° angle of incidence and have a tolerance of ±5% in the designed ratio of reflected power to transmitted power (R/T ratio). This tolerance is unacceptable where each output beam is the result of three beam divisions, as in the present apparatus. Fortunately, the R/T ratio of a plate beam splitter can be adjusted up or down from the nominal value by changing the angle of incidence. The angle giving two beams of equal power or energy being called the "particular incident angle" for a given splitter. Plate beam splitters for visible unpolarized light with nominal R/T ratios of 30/70, 50/50 and 70/30 at 550 nm wavelength are available commercially. Such beam splitters, for example, may consist of a 1-mm thick optical glass coated on one side with a multilayer dielectric partially reflecting film. The opposite side is coated with a multilayer dielectric antireflection film optimized at 45°. These splitters have negligible absorption even at angles greater or smaller than 45° and have withstood a nine watt CW output from a dye laser.

Typical transmittance and reflectance curves are shown in the Melles Griot catalog (Melles Griot 1995/1996 Optics, Opto-mechanics, Lasers and Instruments Catalog, Melles Griot, 1770 Kettering Street, Irvine, Calif. 92714 USA) for unpolarized light from 400 nm to 800 nm. The p-plane and s-plane polarization components of the transmitted beam are also shown ("plane" refers to the plane of incidence, the horizontal plane in this device; "p" denotes polarization parallel to the plane and "s" denotes polarization perpendicular to the plane). These curves demonstrate that plate beam splitters are highly polarization sensitive.

The dye laser beam used in the preferred embodiment is s-plane polarized relative to the plate beam splitter and the wavelength used was 630 nm (this wavelength corresponds to the Photofrin Q-band). According to the Melles Griot catalog, the transmittance of the 30/70 beam splitter is around 50% for an s-plane beam near 630 nm. This was the beam splitter selected for this device (#03BTF011, Melles Griot). Three 50-mm square beam splitters could be cut into twelve 25 mm squares since the dye-laser beam requires only a few square millimeters of surface area. In order to select the seven splitters used in the device of the preferred embodiment, the transmittance and reflectance properties of each square were measured. To do this, each of the splitters (squares) was mounted in turn on a rotary table in front of a dye laser tuned to 630 nm. Two thermopile disc power meters (model 210, Coherent, Pal Alto, Calif.) were used to obtain nearly simultaneous measurements of the reflected and transmitted beams. The dye laser power was set at approximately 500 mW and the R/T ratios were calculated at 1° intervals from 47° through 57°. The 11 measurement pairs for each splitter were repeated and R/T ratios calculated for all 22 pairs. A least squares fit of the 22 R/T ratios to a quadratic equation was solved for the angle that produced an R/T ratio equal to 1. The range of those calculated angles for the 12 splitters was 51.0° to 52.2. Three beam splitters had an R/T ratio of about 1 at 51.5° (this angle was then used in the optical design of the beam splitter device). These splitters were selected for the first splitter 18 and second splitters 19 and 20. Four other beam splitters, each within 3% of the R/T of 1 at an angle of incidence of 51.5, were selected for the final beam splitters 21–24.

Figure 5:
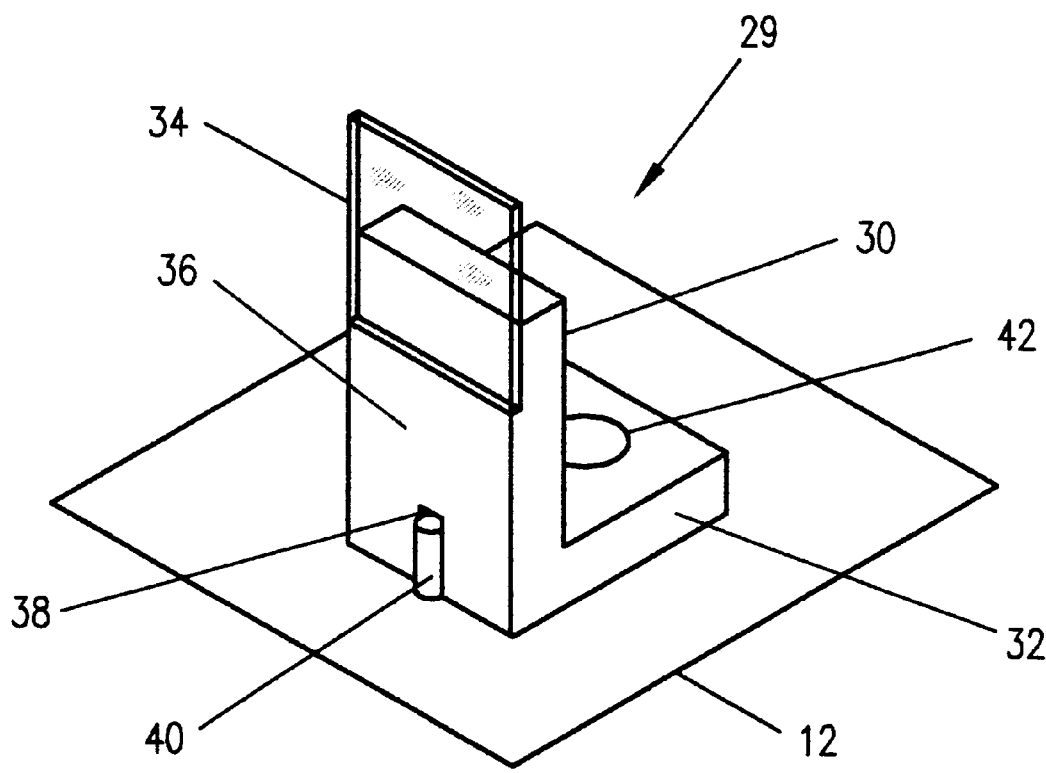
FIG. 5 is a perspective view of a preferred embodiment of a beam splitter and mount used in the invention.

A beam splitter mount 29 shown in FIG. 5 provides beam rotation about a stationary point. The mount was machined from 1.5 inch by 1.5 inch by ¼ inch thick bronze angle 30 and was 1.24 inches high with a 1 inch square base 32. The 1 mm thick beam splitter was cemented to the surface of a 1 mm recess 34 milled into the front 36 of the mount. A 1/16 inch radius groove 38 was milled in the center of the front surface at the base. The vertical axis of a 1/8 inch diameter dowel pin 40 pressed into the optical table 12 passed through the point of incidence of the laser beam on the splitter when the mount was held against the pin. Plastic shim stock was placed under the front or back of the base to provide vertical tilt. The mount was attached to the optical table with a ¼-20 bolt through a Belleville washer and an oversized hole 42 in the base that allowed a few degrees of rotation. The flattened washer exerts a 70 pound force to hold the mount firmly to the optical plate.

Figure 6:
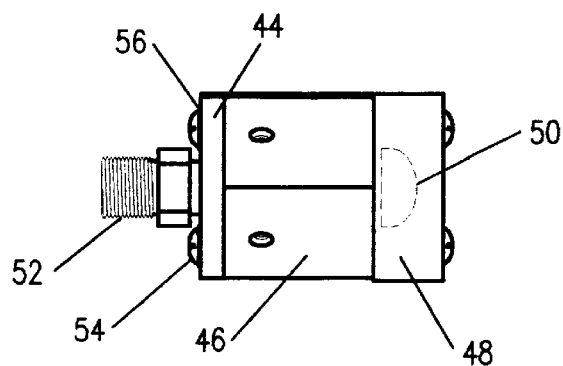
FIG. 6 is a side view of a preferred embodiment of a fiber optic coupler for use in the invention.
Figure 7:
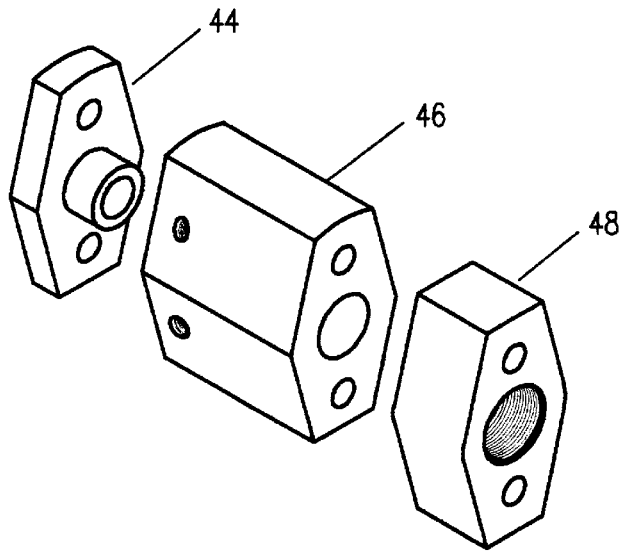
FIG. 7 is a perspective exploded view of the coupler of FIG. 6.
Figure 8:
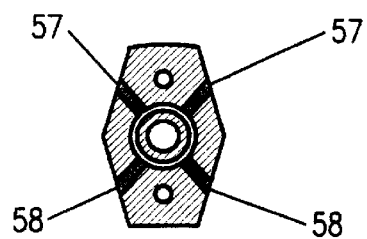
FIG. 8 is a cross-sectional view of the coupler body of the coupler of FIG. 6.

A side view of the assembled fiberoptic coupler is shown in FIG. 6 and an exploded view is shown in FIG. 7. The assembled coupler was 23 mm wide, 38 mm high and 32 mm deep. It included a fiberoptic mounting plate 44 and the coupler body 46, both machined from 1.5 inch diameter brass bar, a model LH-50 lens mount 48 (Newport Corp., Irvine, Calif.). The lens mount 48 was bolted to the front of the coupler body 46 and holds an anti-reflection coated 12.7 mm diameter, 25.4 mm focal length planoconvex lens 50 as indicated in FIG. 6. A fiber which is held in a SMA905 connector is threaded onto mating sleeve 52 and the connector is threaded in or out to provide focusing adjustment. The fiberoptic mount is fastened to the back of the coupler body with two bolts 54 and spring washers 56 through oversized holes. The mating surfaces are polished surfaces so that with a slight tension on the spring washers the optical fiber can be translated in the focal plane by adjusting two upper set screws 57 of an orthogonal pair of opposing set screws 57 and 58 as best seen in cross section in FIG. 8. When the bolts are tightened each flattened washer exerts a 93 pound force. The bottom of each lens mount has a threaded hole for attachment to a Newport compact carrier (model MCC) and microrail (MRL-6). This places the optical plane of the system at approximately 38 mm above the optical plate 12.

The mechanical support of the optical table 12 provides translation, rotation, height adjustment and tilt about two axes to provide for adjustment.

Alignment procedure for the beam splitter apparatus begins with all of the fiberoptic couplers removed. Dye laser power is set as low as possible. The optical table is rotated and translated so that the dye laser beam passes over an input pin, through the unaligned beam splitters 18, 20 and 23, in FIG. 1, and over a pin marking the path of the exit ray. An alignment tool was made from a mounted glass slide with an inscribed vertical line that could be placed directly over an alignment pin. A bolt 61 through a Belleville washer 63 holding table 12 (see FIG. 1) is backed off just so the optical table 12 can be rotated on its base. By successive rotations of the table and translations on a rail carrier the desired alignment can be achieved. When the rail carrier is locked, the Belleville washer flattened and locking hooks engaged, the apparatus is rigidly fixed in place.

The output beam of the dye laser may not be horizontal. In that case the optical table is tilted so that the input beam is parallel to and at a constant height above the plate over the full translation of the rail carrier. The correct height is obtained when the input laser beam passes without vertical displacement through the lens of a first coupler 60 positioned on a short segment microrail 65. Several cycles of plate rotation, translation, tilt and height adjustments are required to achieve a perfect alignment. Coupler 60 is then removed and all plate adjustment controls are locked with the input beam passing over the input alignment pin and over the output alignment pin. The location of the beam is marked on a far target and coupler 60 is positioned so that an expanded beam produced by the coupler lens is centered on a target.

Setting the angle of incidence on the beam splitters is the next step in the alignment. Beam splitter 18 is rotated to aim the reflected input beam through splitters 19 and 21 and over a pin marking the exit ray. The beam location on a far target is marked. Coupler 62 is positioned on a microrail 69 to align the expanded beam with a target. Any vertical displacement of the output beam on the target is noted. The coupler is removed and the beam splitter mount is wedged with small tabs cut from plastic shim stock to correct for any beam tilt. A new beam location on the target is marked and the alignment to the coupler is repeated until the expanded beam is centered on the target. This process is repeated for the other 6 beam splitters in the following sequence: splitters 19 and 20 with couplers 64 and 66, splitters 21 and 23 with couplers 68 and 70, and splitters 22 and 24 with couplers 72 and 74.

When the laser beam enters the optical fiber connected to coupler 60 light is reflected from the output face of the fiber. This light travels back through the fiber and the coupler lens and is reflected from beam splitters 23, 20 and 18 toward a beam stop fastened to the side of the optical table. The coupler lens forms the three images on the beam stop of the input face of the quartz fiber and the bright impingement point of the focused beam. These images can be brought to a sharp focus by adjusting the SMA mating sleeve 52. If the bright impingement point is not centered on the image of the fiber face it is made to do so with the two upper set screws 57 in the coupler body 46. A piece of tape is put over the lens mount of coupler 60 in order to block its set of images and the alignment procedure is repeated for the next optical fiber.

Figure 2:
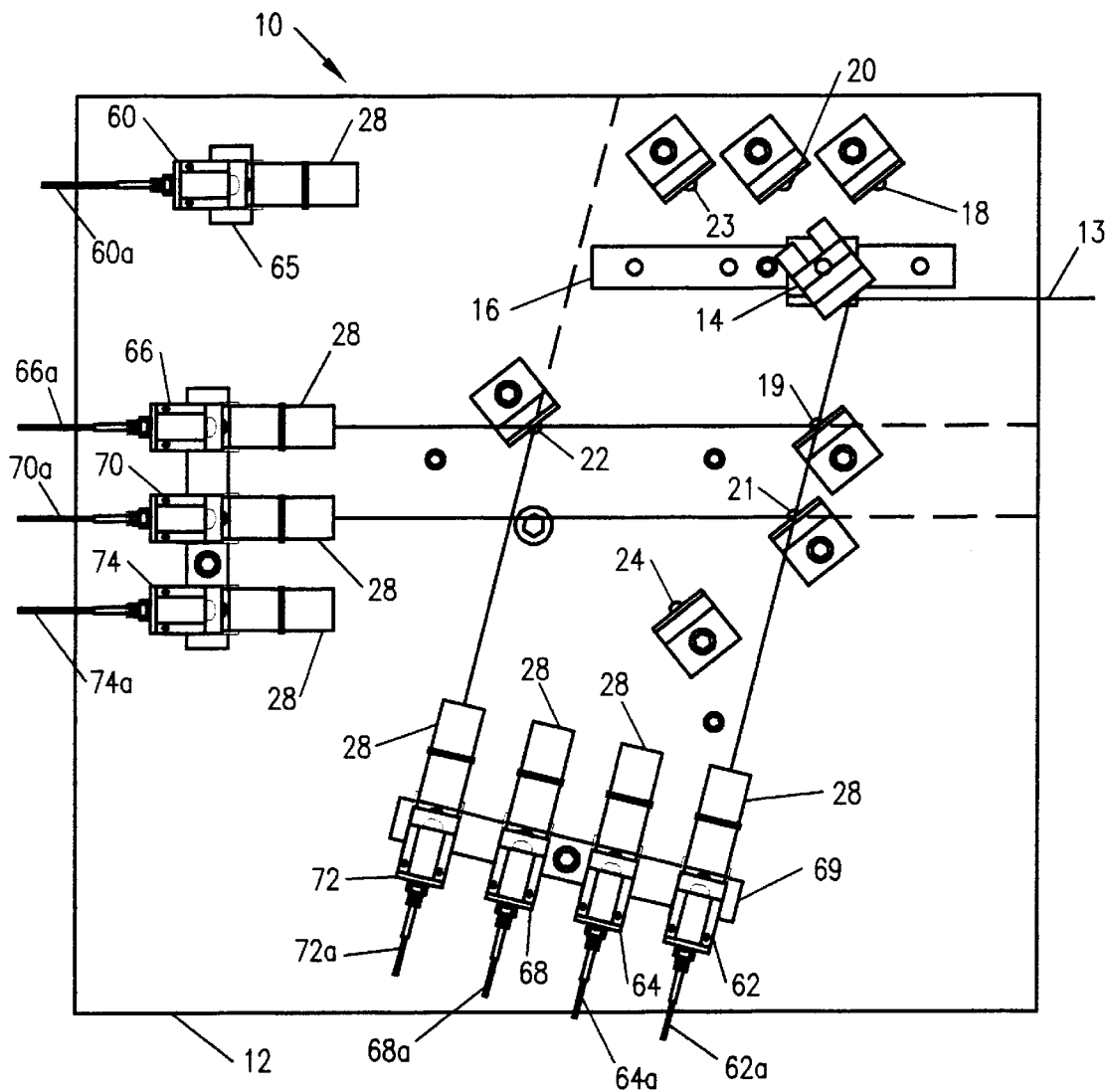
FIG. 2 shows a top view of an embodiment of the invention arranged to provide four output beams.
Figure 3:
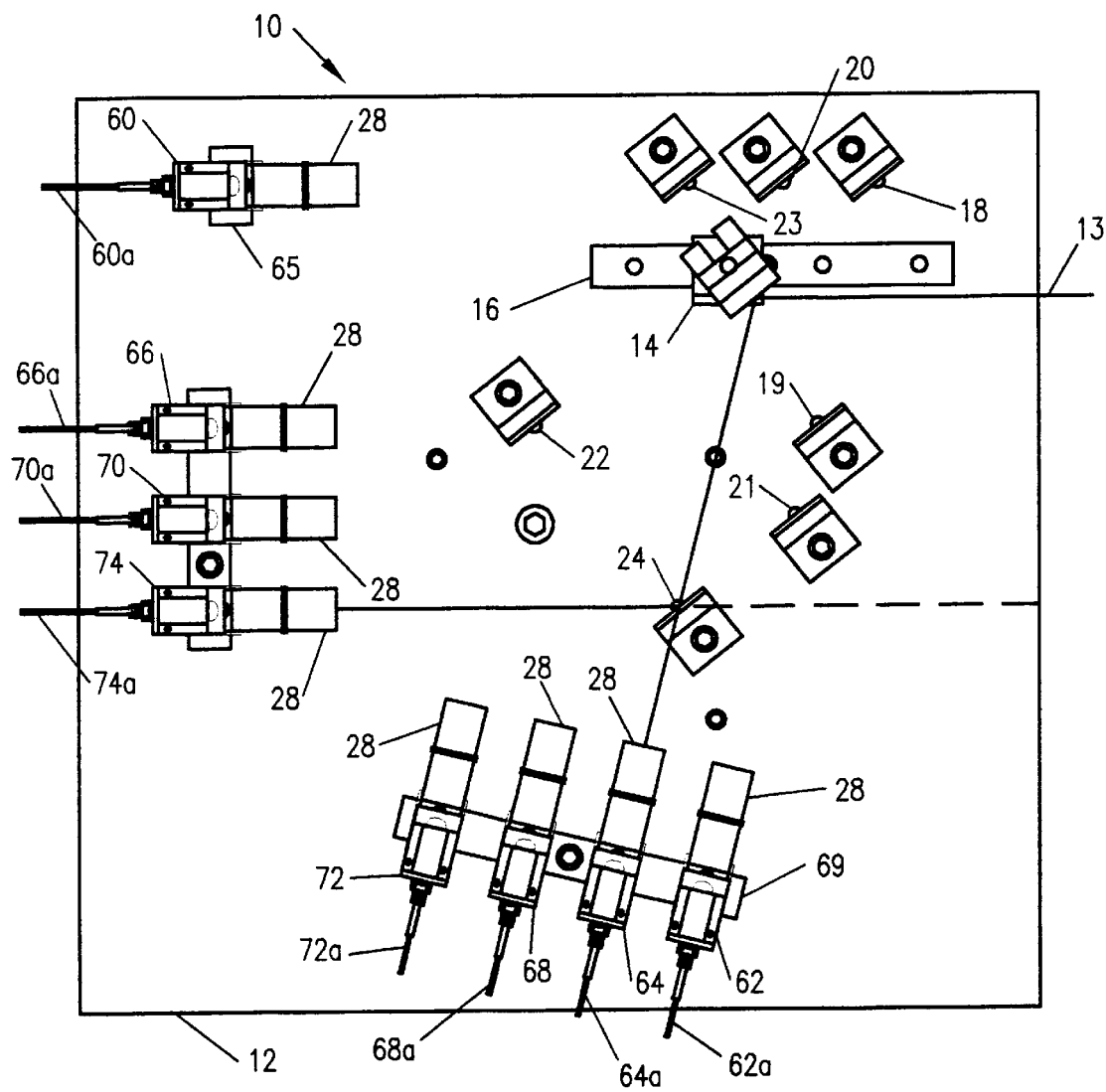
FIG. 3 shows a top view of an embodiment of the invention arranged to provide two output beams.
Figure 4:
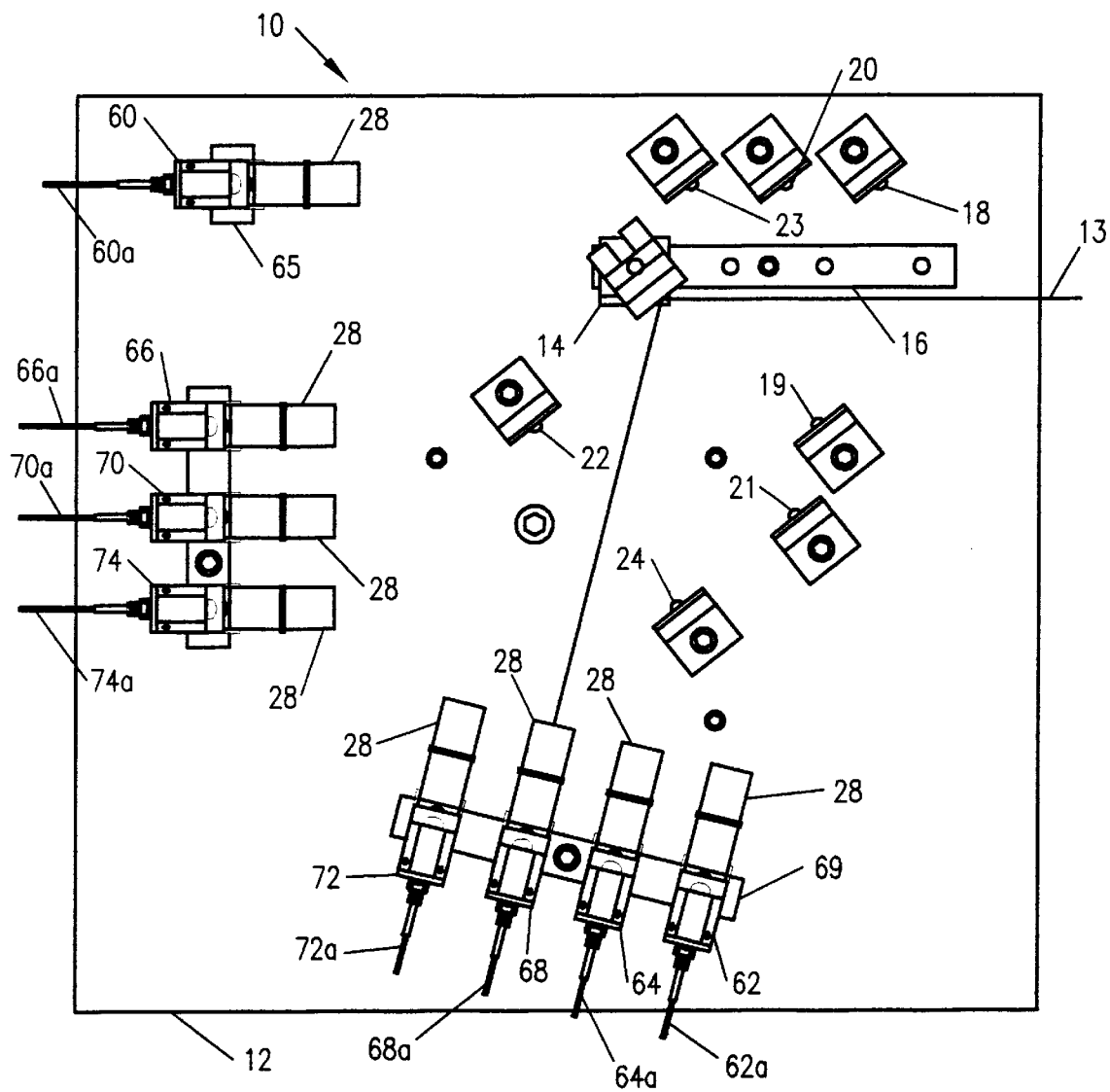
FIG. 4 shows a top view of an embodiment of the invention arranged to provide a single output beam.

Finally, the optical table can be translated to the 4-2-1 fiber position as shown in FIGS. 2–4 using an alignment tool to place the laser beam over the dowel pin. The fold mirror 14 mounted on a compact carrier is placed on the microrail 16 so that the reflected beam passes through beam splitters 19 and 20. By translating the mirror and aiming the reflected beam with the mirror controls, the same set of images, from fibers attached to couplers 62, 66, 70 and 72, will appear on the beam stops. Then, images from fibers 64a and 74a will appear just by translating the fold mirror 14 on the microrail 16 to the correct position. Moving the mirror further down the rail 16 will not produce an image when the laser is coupled to fiber 68a, but the reflected light can be seen at the output coupler of the dye laser. Alternatively, a glass slide can be held in the reflected beam so that the image appears on a beam stop between beam splitters 21 and 24.

When one beam is wanted only coupler 60 is used. When two beams are wanted couplers 64 and 74 are used, and when four beams are needed couplers 62, 66, 70 and 72 are involved.

The power of each of the eight beams was measured by placing a thermopile power meter distal to each optic mount. Both the optical fibers and the Brewster window attenuators were removed, leaving only the focusing lenses in the mounts. In the first set of measurements the output of the dye laser (input to the beam splitter device) was set to 1400 mW of 630 nm light. Because of some small drifts in the laser output, the power was adjusted 2 times and measured 13 times during the course of the data collection, where the average ±S.E.M. total power was calculated as 1380.9±18.1 mW. The power of each individual beam was measured 11 times and averaged (Table 1). The highest and lowest (average) measurements of the split beams differed by only 2%. The sum of the average powers of the eight split beams was 1376.5 mW, indicating <1% loss through the beam splitter device. For the second set of measurements, the dye laser power was set to 6100 mW. The power was set once and measured 11 times, where the average ±S.E.M. total power was 6035.0±77.6 mW. Highest and lowest measurements, averaged over 10 measurements/individual beam, differed by <3%. The sum of the eight averaged powers was 5749.1 mW. This represents <5% loss of power through the device.

The main utility of the beam splitter apparatus of the invention is to convert what would otherwise be a laborious and time consuming procedure into an acceptable and practical treatment. For example, photodynamic therapy for treatment of patients with numerous basal cell tumors of the skin as a result of a genetic defect (nevoid basal cell carcinoma syndrome) is highly effective and desired by these patients because of often superior cosmetic outcomes compared to surgical procedures. Because each tumor or site must be exposed to therapeutic light for approximately 24 min., the sequential treatment of 40–50 lesions (as commonly presented) is completely impractical. The ability to treat 8 such lesions or sites simultaneously by using the beam splitter and specially designed fiber positioners makes this a practical and acceptable procedure for these patients and others with a large number of skin lesions.

TABLE 1

Distribution of Power Following an 8-Way Split of 1400 mW and 6100 mW 630 nm Laser Light

| | 1[a] | 2 | 3 | 4 | 5 | 6 | 7 | 8 |
|---|---|---|---|---|---|---|---|---|
| 1400 mW[b] | 174.5 ± 3.8[d] | 172.3 ± 3.1 | 170.2 ± 3.9 | 172.1 ± 3.6 | 170.9 ± 4.1 | 172.5 ± 3.5 | 170.8 ± 3.3 | 173.2 ± 3.4 |
| 6100 mW[c] | 727.0 ± 7.8[e] | 717.0 ± 5.9 | 713.2 ± 1.2 | 717.8 ± 8.1 | 710.1 ± 7.6 | 722.0 ± 7.7 | 716.6 ± 7.2 | 725.4 ± 5.5 |

[a]Numbers correspond to each of eight split beams shown in FIG. 1
[b]Nominal dye laser output (i.e., beam splitter device input) power. Due to laser drift the average ± S.E.M. power, measured 13 times over the course of the data collection was 1380.9 ± 18.1 mW
[c]Nominal dye laser output. Average ± S.E.M. power, measured 11 times during data collection, was 6035 ± 77.6 mW
[d]Average ± S.E.M. power, in mW, for 11 different measurements of each individual beam. Power was measured distal to each optic mount (FIG. 1, components 1–8). Optical fibers and Brewster window attenuators were removed before measurement; focusing lenses were left in place
[e]Average S.E.M. power, in mW, for 10 different measurements of each beam as described above

What is claimed is:

1. A laser beam splitter apparatus capable of forming at least eight output laser beams from a laser input, said splitter comprising:

an arrangement of at least seven beam splitters each of which splits an incident laser beam into two exit beams of equal energy at a particular incident angle for each splitter, at least some of said particular incident angles being different from each other for the different splitters, said apparatus comprising a first splitter, having a first splitter particular incident angle, and being arranged for receiving said laser input at the first particular incident angle;

said second and third splitters having second and third particular incident angles, and being arranged so that the exit beams of the first splitter are directed to the second and third splitters, as their incident laser beams at the first particular incident angle;

each of said second and third splitters providing two exit beams when receiving an incident laser beam;

said fourth, fifth sixth and seventh splitters, having fourth, fifth, sixth and seventh particular incident angles, and being arranged so that the exit beams from said second and third splitters are directed to said fourth, fifth, sixth and seventh splitters at the first particular incident angle as their incident laser beam;

each of said fourth, fifth, sixth and seventh splitters providing two exit laser beams when receiving an incident laser beam;

the second and third particular incident angles being closer to the first particular incident angle than the fourth, fifth, sixth and seventh particular incident angles, the variance in energy between the two exit beams of each of the first, second and third splitters being less than about 3 percent at an incident laser beam angle about equal to the first particular incident angle and the variance in energy between the two exit beams of each of the fourth, fifth, sixth, and seventh splitters being less than about 7 percent at an incident laser beam angle about equal to the first particular incident angle, said apparatus being capable of providing at least eight output beams varying in energy from each other by less than about 10 percent.

2. The apparatus of claim 1 further comprising at least one additional beam splitter for receiving one of the eight output beams from one of the fourth, fifth, sixth and seventh splitters to provide a total number of output beams from the apparatus in excess of eight.

3. The apparatus of claim 1 wherein the variance in energy between the two exit beams of each of the first, second and third splitters is less than about one percent at an incident laser beam angle about equal to the first particular incident angle and the variance in energy between the two exit beams of each of the fourth, fifth, sixth, and seventh splitters being less than about 5 percent at an incident laser beam angle about equal to the first particular incident angle, said apparatus being capable of providing at least eight output beams varying in energy from each other by less than about 5 percent.

4. The apparatus of claim 1 where in the variance in energy between the two exit beams of each of the first, second and third splitters is less than about 0.5 percent at an incident laser beam angle about equal to the first particular incident angle and the variance in energy between the two exit beams of each of the fourth, fifth, sixth, and seventh splitters being less than about 1.5 percent at an incident laser beam angle about equal to the first particular incident angle, said apparatus being capable of providing at least eight output beams varying in energy from each other by less than about 3 percent.

5. The apparatus of claim 1 wherein the apparatus further comprises an adjustable redirecting means for intercepting said laser input and redirecting it away from said first splitter.

6. The apparatus of claim 5 wherein the redirecting means is adjusted to redirect the laser input away from all splitters to provide an apparatus output of a single laser beam.

7. The apparatus of claim 5 wherein the redirecting means is adjusted for intercepting said laser input and redirecting it toward one of the fourth, fifth, sixth and seventh splitters to provide an apparatus output of two laser beams.

8. The apparatus of claim 5 wherein the redirecting means is adjusted for intercepting said laser input and redirecting it toward one of the second and third splitters to provide an apparatus output of four laser beams.

9. The apparatus of claim 5 wherein the redirecting means comprises a mirror having at least four adjustable positions wherein:

position one intercepts the laser input to reflect the beam away from the splitters to provide an apparatus output of a single laser beam;

position two intercepts the laser beam to reflect it toward one of the fourth, fifth, sixth, and seventh splitters to provide an apparatus output of two laser beams;

position three intercepts the laser beam to reflect it toward one of the second and third splitters to provide an apparatus output of four laser beams; and position four permits the input beam to strike the first splitter at the first splitter particular incident angle to provide an apparatus output of eight laser beams.

10. The apparatus of claim 1 wherein fiber optic couplers are provided in paths of the apparatus output laser beams to receive the energy of such beams and for directing beam energy through a fiber optic.

11. The apparatus of claim 10 wherein said couplers provide a back reflection beam having an energy of from about 2 to about 6 percent of the energy received from an output beam.

12. The apparatus of claim 11 including means for aligning the output beams with the couplers by varying the position of said couplers relative to an image formed by their back reflection beams.

13. A method for providing laser treatment to a patient by simultaneously directing a plurality of laser beams from fiber optics receiving laser energy from the apparatus of claim 1 to areas on a patient in need of laser treatment.

14. A method for providing laser treatment to a patient by simultaneously directing a plurality of laser beams from fiber optics receiving laser energy from the apparatus of claim 2 to areas on a patient in need of laser treatment.

15. A method for providing laser treatment to a patient by simultaneously directing a plurality of laser beams from fiber optics receiving laser energy from the apparatus of claim 3 to areas on a patient in need of laser treatment.

16. A method for providing laser treatment to a patient by simultaneously directing a plurality of laser beams from fiber optics receiving laser energy from the apparatus of claim 4 to areas on a patient in need of laser treatment.

17. A method for providing laser treatment to a patient by simultaneously directing a plurality of laser beams from fiber optics receiving laser energy from the apparatus of claim 5 to areas on a patient in need of laser treatment.

18. A method for providing laser treatment to a patient by simultaneously directing a plurality of laser beams from fiber optics receiving laser energy from the apparatus of claim 9 to areas on a patient in need of laser treatment.

19. A method for providing laser treatment to a patient by simultaneously directing a plurality of laser beams from fiber optics receiving laser energy from the apparatus of claim 10 to areas on a patient in need of laser treatment.

20. Use of the apparatus of claim 1 as at least a part of a light delivery system for photodynamic therapy.

21. Use of the apparatus of claim 2 as at least a part of a light delivery system for photodynamic therapy.

22. Use of the apparatus of claim 3 as at least a part of a light delivery system for photodynamic therapy.

23. Use of the apparatus of claim 5 as at least a part of a light delivery system for photodynamic therapy.

24. Use of the apparatus of claim 9 as at least a part of a light delivery system for photodynamic therapy.

25. Use of the apparatus of claim 10 as at least a part of a light delivery system for photodynamic therapy.

* * * * *

UNITED STATES PATENT AND TRADEMARK OFFICE
CERTIFICATE OF CORRECTION

PATENT NO.      : 6,084,717
DATED           : July 4, 2000
INVENTOR(S)     : Leroy M. Wood et al.

It is certified that error appears in the above-identified patent and that said Letters Patent is hereby corrected as shown below:

<u>Column 1,</u>
Line 2, before the Background of the Invention, insert -- This invention was made with United States government support under Grant PO1 CA55791 from the NIH. The United States government may have certain rights in this invention. --

Signed and Sealed this

Eighth Day of April, 2003

JAMES E. ROGAN
*Director of the United States Patent and Trademark Office*